United States Patent [19]
Andrulis, Jr.

[11] Patent Number: 5,434,170
[45] Date of Patent: Jul. 18, 1995

[54] METHOD FOR TREATING NEUROCOGNITIVE DISORDERS

[75] Inventor: Peter J. Andrulis, Jr., Bethesda, Md.

[73] Assignee: Andrulis Pharmaceuticals Corp., Beltsville, Md.

[21] Appl. No.: 172,155

[22] Filed: Dec. 23, 1993

[51] Int. Cl.6 ............................................. A61K 31/445
[52] U.S. Cl. ....................... 514/323; 514/171; 514/264; 514/297; 546/105; 546/200; 546/201
[58] Field of Search ............... 546/105, 200; 514/171, 514/264, 297, 323

[56] References Cited

U.S. PATENT DOCUMENTS

| | | | |
|---|---|---|---|
| 2,830,991 | 4/1958 | Keller et al. | 546/200 |
| 4,816,456 | 3/1989 | Summers | 514/255 |
| 4,839,364 | 6/1989 | Shutske et al. | 514/290 |
| 5,210,087 | 5/1993 | Shutske et al. | 514/297 |
| 5,318,967 | 6/1994 | Bruderer et al. | 514/232.8 |

*Primary Examiner*—Richard L. Raymond
*Attorney, Agent, or Firm*—Isaac A. Angres

[57] ABSTRACT

A method for treating a central nervous system or peripheral nervous system cholinergic deficit state in a mammalian organism in need of such treatment, said method comprising administering to said mammal an amount of thalidomide effective in the treatment of a cholinergic deficit state and for a time sufficient to achieve a suitable blood level to treat said cholinergic deficit state.

28 Claims, No Drawings

METHOD FOR TREATING NEUROCOGNITIVE DISORDERS

The present invention is directed to compositions, and methods for alleviating the symptoms associated with neurocognitive disorders, i.e., senile dementia of the Alzheimer's type. In one specific aspect, the present invention is directed to a method for treating Alzheimer's disease with thalidomide.

In another specific embodiment of the invention, senile dementia is treated with thalidomide in conjunction with nonsteroidal anti-inflammatory carboxylic acids selected from the group consisting of the aryl acetic acids, the aryl propionic acids, the salicylates, the ferramic acids, the biphenyl carboxylic acids and the diphenylether carboxylic acids.

BACKGROUND OF THE INVENTION

Thalidomide (N- phthalidoglutarimide) was first synthesized in 1953 by researchers at Chemie Grunenthal in Germany. It was marketed in Europe in 1956 as a sedative/hypnotic drug. Thalidomide is orally administered. It is poorly absorbed in humans. When 100 to 200 milligrams (mg) of thalidomide is ingested by humans, a maximal blood concentration of 0.9 to 1.5 mg/liter is attained 4 to 6 hours later. Thalidomide is extensively distributed throughout the body but does not selectively localize in any tissue. Thalidomide breaks down by spontaneous hydrolysis; however, the hydrolyric cleavage in serum is much slower than in vitro at pH 7.4. This may be due to thalidomide being highly bound to plasma proteins. Thalidomide metabolites are renally excreted. In a series of animal studies, racemic thalidomide has not been toxic. However, side effects in humans have included somnolence, teratogenicity and, upon extended administration, peripheral neuropathy. The teratogenic potential of thalidomide resulted in a variety of malformations of fetuses (phocomelia) and the subsequent removal of thalidomide from the market. The mechanism of the teratogenic effect is not known; however, it will occur when thalidomide is taken between the 35th and 50th day of the menstrual age of the embryo.

In addition to the sedative effect, thalidomide has exhibited an immunomodulatory effect which has resulted in its therapeutic use in the following conditions: rheumatoid arthritis, acute and chronic graft versus host disease, aphthosis, cold hemagglutinin disease, colitis, cutaneous lupus erythematosus, erythema nodosum leprosum, erythema multiform, histiocytosis, immune complex vasculitis, Jessner-Kanof's disease, lichen planus, pemphigoid disorders, photodermatoses, prurigo nodularis, pyoderma gangrenosum, sarcoidosis and Weber Christian's disease. The exact immunomodulatory effect of thalidomide on a molecular level has not been determined; however, a number of observations in this regard have been made. Coulsen et al. (*Clin. Exp. Immunol.*, 7:241, 1970) showed thalidomide derivatives could inhibit production of transformed cells in mixed lymphocyte culture, whereas the lymphocyte response to phytohemagglutinin was not inhibited. In another study by Moncada et al., (*Int. J. Leprosy*,:53:209,1985) thalidomide was associated with increases in previously suppressed CD4 lymphocyte counts in erythema nodosum leprosum. Thalidomide has also been observed by Sampaio et al. (*J. Exp. Med.*, 173:699, 1991) to inhibit tumor necrosis factor alpha production by stimulated monocytes. Elevated levels of tumor necrosis factor alpha in erythema nodosum leprosumwere reduced by treatment with thalidomide (Sampaio et al., *J. Exp. Med.*, 175:1729, 1992). Tumor necrosis factor alpha has been demonstrated to induce expression of HIV from cell lines (Poli et al., *Proc. Nat. Acad. Sci., USA*, 87:782, 1990). Blood tumor necrosis factor levels are high in HIV-infected individuals (Lahdevirta et al., *Am. J. Med.*, 85:289, 1988). Thalidomide has been shown to reduce HIV production in peripheral blood mononuclear cells of HIV-infected patients. Thalidomide also inhibited HIV expression from infected cells lines induced with tumor necrosis factor alpha (Schauf et al., *Intl. Sci. Conference on Antimicrobial Agents and Chemotherapy*, Anaheim, Calif., 1992).

Two million Americans have senile dementia of the Alzheimer's type. It accounts for greater than 50% per cent of dementias in the elderly. About 60% of this population are in long- term care facilities. Alzheimer's disease is the fourth leading cause of death in Americans over the age of 65. The etiology of Alzheimer's disease may be familial in 50% of cases and sporadic in the other 50%. Alzheimer's disease is divided into three clinical stages. Stage one is characterized by a memory loss and emotional instability. The frequency of misdiagnosis at this stage is high. In the second stage, patient confusion increases and although patients are ambulatory, they are at significant risk for falls and accidents. In the last stage of the disease, patients begin to lose control over bodily functions. They become completely dependent on caregivers and are at high risk for development of pneumonia, malnutrition and pressure necrosis of the skin. The patient ultimately goes into a coma and dies. Senile dementia of the Alzheimer's type is characterized by a degenerative process in which there is a loss of cells from the cerebral cortex, hippocampus and subcortical structures. There is the presence of neuritic or senile plaques which are areas of degenerating nerve terminals surrounding cores of aggregated and insoluble protein. This protein, termed $\beta$eta-amyloid peptide, is a 40 to 42 amino acid peptide derived from a larger amyloid precursor protein. Many researchers believe that excessive deposition of this toxic protein in the brain results in tissue damage and the development of Alzheimer's disease. However evidence has been recently put forward that Alzheimer's disease may be a chronic inflammatory disorder similar to arthritis. $\beta$eta-amyloid deposits in the brain may trigger an inflammatory response resulting in the destruction of both damaged and healthy nerve tissue (Schnabel, *Science*, 260:1719, 1993).

A number of investigators have observed that the brains of patients with Alzheimer's disease exhibit many of the classical markers of immune-mediated damage. These have included increased numbers of microglia (cells believed to be the functional equivalent to macrophages in the central nervous system) (Stryren et al., *Exp. Neurel.*, 110:93, 1990) and astrocytes expressing inflammatory reactants interleukin 1 and alpha 1 antichymotrypsin (Abraham et al., *Cell*, 52:487, (1988). Complement proteins of the classical pathway have been immunohistochemically detected in Alzheimer's brain tissue and are most often associated with the $\beta$eta amyloid plaques. Rogers et al., (*Proc. Nat. Acad. Sci., USA*, 89:10016, 1992) presented evidence that $\beta$eta amyloid protein activates the classical complement pathway without mediation of immunoglobulin, thereby contributing to the development of the inflammatory process. In another study by Fillit et al., (*Neurosci. Lett.*, 129:318, 1991) levels of tumor necrosis factor alpha were measured in both patients with Alzheimer's disease and age-matched controls by enzyme-linked immunosorbent assay and cytotoxicity bioassay.

The authors reported elevated levels of tumor necrosis factor in Alzheimer's patients compared to controls and indicated elevated circulating tumor necrosis factor may be derived from the local central nervous system inflammatory reaction found in Alzheimer's patients and may account for some of the systemic manifestations of Alzheimer's disease such as weight loss.

McGeer hypothesized that if this inflammatory reaction was an important part of the pathology of Alzheimer's disease, then patient groups with autoimmune diseases such as rheumatoid arthritis who are on a course of anti-inflammatory drugs for a prolonged period of time should have a reduced incidence of Alzheimer's disease. McGeer et al., (*Lancet*, 335:1037, 1990) retrospectively reviewed hospital data covering 12,000 patients over the age of 64 to determine the prevalence of Alzheimer's disease in rheumatoid arthritis patients. They found that while the prevalance of Alzheimer's disease in the general population was taken to be 2.7%., only 0.39% of those patients with rheumatoid arthritis also had Alzheimer's disease. These data could be interpreted to indicate that anti-inflammatory therapy in patients with rheumatoid arthritis resulted in an unusually low prevalence of Alzheimer's disease. In another study by McGeer et al., (*Dementia*, 3:146, 1992) of 4000 leprosy patients there was 2.9% incidence of dementia in those patients taking the leprosy drug Dapsone which has an anti-inflammatory effect versus an incidence of 6.25% in those lepers who had not taken Dapsone for five years. These results indicate the possibility that anti-inflammatory drugs may have an effect on the development of Alzheimer's disease. As previously stated, thalidomide has an inhibitory effect on the synthesis of tumor necrosis factor alpha, a mediator of the inflammatory reaction and which is elevated in the sera of Alzheimer's patients (Fillit, *Neurosci. Lett.*, 129:318, 1991). Corder et al (Sci 261: 921, 1993) have discovered an association between Alzheimer's disease and the apolipoprotein E locus on human chromosome 19. Apolipoprotein E (APOE) is a protein that transports cholesterol through the blood stream. APOE has three alleles, APOE-$\epsilon$2, APOE-$\epsilon$3 and APOE-$\epsilon$4. Risk for late onset Alzheimer's disease, which starts after age 65 and comprises three quarters of all cases, increased from 20% to 90% and the mean age of onset decreased from 84 to 68 years in patients with an increasing number of APOE-$\epsilon$4 alleles. The APOE-$\epsilon$4 allele may either have an active pathogenic role in Alzheimer's disease development or may only be closely linked on chromosome 19 to a gene that does. However it is unusual in the case of a genetic linkage for the APOE gene dose to be correlated with development of Alzheimer's disease. APOE-4 binds more rapidly and tighter to beta amyloid than other APOE's and it is hypothesized that APOE-4 causes soluble circulating beta-amyloid to become insoluble upon binding to it and thereby facilitating beta-amyloid deposition in brain tissue resulting in plaque formation. Soluble beta-amyloid also binds to another apolipoprotein, APOJ. It has been hypothesized that binding to APOJ protects beta-amyloid's solubility and that the amount of APOE-4 versus APOJ is in a delicate balance in the brain with Alzheimer's disease developing if the APOE gene dose is able to shift the balance in favor of APOE-4. APOE-4 also binds to the neurofibrillary tangles found in the brain tissue of patients with Alzheimer's disease. The significance of this is not clear at this time. Progress of Alzheimer's disease is believed to be attributed to degeneration of certain nerve tracts in the central nervous system, resulting in the loss of associated functions. Pathological studies indicate that brains of Alzheimer's patients have loss of several neurotransmitter systems, related to different functions, but the system which is implicated the most is the cholinergic system. Studies show that several important cholinergic tracts innervating the cortical and hippocampal regions degenerate. Although this particular degeneration may not account for all the symptoms of Alzheimer's, it may account for the cognitive and memory deficits, which are some of the most difficult symptoms for patients and their families to deal with. The prior art is silent regarding the treatment of cognitive disorders with thalidomide.

SUMMARY OF THE INVENTION

The primary object of the present invention is the treatment of neurocognitive disorders by administering thalidomide to a patient in need of such treatment.

Another object of the present invention is to provide a therapeutic method for alleviating the symptoms of cognitive decline by administering a therapeutically effective amount of thalidomide.

An additional object of the present invention is to treat Alzheimer's disease with a therapeutically effective amount of thalidomide.

Another object of the present invention is to treat Alzheimer's disease or neurocognitive disorders with thalidomide in combination with other drugs.

A further object of the invention is to treat Alzheimer's disease with a pharmaceutical composition comprising thalidomide and a non-steroidal anti-inflammatory carboxylic acid.

Still another object of the invention is to treat Alzheimer's disease with a pharmaceutical composition comprising thalidomide and a separate pharmaceutical composition comprising a non-steroidal anti-inflammatory carboxylic acid.

Another object of the invention is to treat Alzheimer's disease with pharmaceutical composition comprising thalidomide and a steroidal anti-inflammatory.

Still another object of the invention is to treat Alzheimer's disease with a pharmaceutical composition comprising thalidomide and separate pharmaceutical composition composition comprising a steroidal anti-inflammatory carboxylic acid.

The present inventor has now discovered a method for treating central nervous system or peripheral nervous system cholinergic deficit states in a mammal. The method comprises administering to a mammal an amount of thalidomide alone or in combination with compounds selected from the group consisting of tacrine, non-steroidal anti-inflammatory carboxylic acids (NSAIDs), $\beta$-amyloid inhibitors and pentoxyphylline effective in the treatment of cholinergic deficit states and for a time sufficient to achieve a suitable blood level to treat said cholinergic deficit state.

The present inventor has also discovered a pharmaceutical composition of matter for treating said cholinergic deficit states in a mammalian organism in need of such treatment, said composition comprising a unit dosage amount of thalidomide alone or in combination with the above mentioned compounds and pharmaceutically acceptable carrier.

DESCRIPTION OF THE PREFERRED EMBODIMENTS

The present invention deals with a method for treating a central nervous system or peripheral nervous system cholinergic deficit state in a mammalian organism in need of such treatment, said method comprising administering to said mammal an amount of thalidomide effective in the treatment of a cholinergic deficit state and for a time sufficient to achieve a suitable blood level to treat said cholinergic deficit state.

Additionally, the present invention relates to a method of treating the symptoms of cognitive decline in a mammal which comprises administering to a mammal affected with said cognitive decline a therapeutically effective amount of thalidomide.

Furthermore, the present invention provides a method of treating a mammal suffering from cognitive decline with thalidomide and independently with other agents selected from the group consisting of tacrine, non-sterodial anti-inflammatory agents, sterodial anti-inflammatory agents, β-amyloid inhibitors and/or pentoxyphylline.

The invention also provides a method for treating the symptoms of cognitive decline in a mammal which comprises administering to a mammal affected with said cognitive decline a therapeutically effective amount of a mixture of thalidomide with a compound selected from the group consisting of tacrine, non-steroidal anti-inflammatory carboxylic acids (NSAIDs), β-amyloid inhibitors and pentoxyphylline.

The present invention further provides a method for treating Alzheimer's disease in a mammal, said method comprising administering to said mammal a therapeutically effective amount of thalidomide.

The therapeutically effective amounts of thalidomide are typically 30 mg to 1000 mg and preferably 100 mg to 500 mg.

When thalidomide is used in combination with NSAIDs or sterodial anti-inflammatories (SAIDs), the amount of thalidomide is typically in the range of about 30 mg to about 1000 mg while the NSAIDs are present in the range of about 200 mg to 800 mg and the SAIDs are present in the range of 10 mg to 60 mg. For example, an effective combination for treating Alzheimer's is a gelatin capsule containing 200 mg of thalidomide and 200 mg of ibuprofen given three times daily. Two capsules each containing the active ingredient may also be prescribed.

The precise amount of thalidomide alone or with the other active materials mentioned above will vary depending, for example, on the condition for which the drug is administered and the size and kind of the mammal. Generally speaking, the thalidomide can be employed in any amount effective in the treatment of central nervous system or peripheral nervous system cholinergic deficit states. The symptoms of these states, including senile dementia of the Alzheimer's type are improved.

For humans, typical effective amounts of thalidomide for use in the unit dose compositions of the present invention range from about 30 mg to 1000 mg per 24 hours; however greater amounts may be employed, if desired. This range is based on administration to a 70 Kg human. A preferred amount is 100 mg to 800 mg.

The more preferred range contains about 100 mg to 500 mg of thalidomide per 24 hours.

As mentioned above, thalidomide may be given alone or in combination with other drugs which are also useful in the treatment of central nervous system or peripheral nervous system cholinergic deficit states.

For example, when thalidomide is used with tacrine, a typical formulation contains from about 100 mg to 500 mg of thalidomide and from about 100 mg to 300 mg of tacrine. The formulations are administered over a 24 hour period. When thalidomide is combine with NSAIDs or steroidal anti-inflammatories, a typical formulation contains from about 100 mg to about 500 mg of thalidomide, and from about 100 mg to 800 mg of NSAIDs or 10 mg to 60 mf of SAID. The preferred non-steroidal anti-inflammatory is selected from the group consisting of aryl propionic acids, aryl acetic acids, biphenyl carboxylic acids, diphenylether carboxylic acids, the salicylates, and the fenamic acids.

The non-steroidal carboxylic acids can be chracterized into four groups:

(1) The propionic acid derivatives; (2) the acetic acid derivatives; (3) the fenamic acid derivatives; and (4) the biphenylcarboxylic acid derivatives or a pharmaceutically acceptable salt thereof.

The propionic acid derivatives which may be used comprise: ibuprofen, ibuprofen aluminum, indoprofen, ketoprofen, naproxen, benoxaprogen, flurbiprofen, fenoprofen, fenbufen, pirprogen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and anti-inflammatory properites are also intended to be included in this group.

Thus, "propionic acid derivatives" as defined herein are nonnarcotic analgesics/non-sterodial anti-inflammatory drugs having a free —CH(CH$_3$)COOH or —CH$_2$CH$_2$COOH group (which optionally can be in the form of pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenflozic acid. Structurally related acetic acid derivatives having similar analgesic and anti-inflammatory properties are also intended to be encompassed by this group.

Thus, "acetic acid derivatives" as defined herein are non-narcotic analgesics/non-sterodidal anti-inflammatory drugs having a free —CH$_2$COOH group (which optionally can be in the form of a pharmaceutically acceptable salt group, e.g., —CH$_2$COO$^-$Na$^+$), typically attached directly to a ring system.

The fenamic acid derivatives which may be used comprise: mefanamic acid, meclofenamic acid, flufenamic acid, niflumic acid, and tolfenamic acid. Structurally related fenamic acid derivatives having similar analgesic and anti-inflammatory properties are also intended to be encompassed by this group.

Thus, "fenamic acid derivatives" as defined herein are non-narcotic analgesic/non-steroidal anti-inflammatory drugs which contain the basic structure:

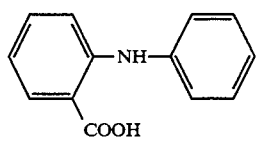

which can bear a variety of substitutents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

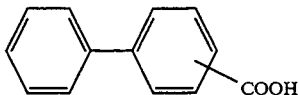

which can bear a variety of substitutents and in which the free —COOH group can be in the form of a pharmaceutically acceptable salt group, e.g., —COO—Na +. Typical acids include ibuprofen, diflumisol, fenoprotenin acid, meclofenic acid, mefenamic acid, naproxen, suliudor, indomethacon, talmetin, fenbufen, ketoprofen, indoprofen, fluprofen, benozaynofen, pirprofen, miroprofen, thioxaprofen, aspirin, choline magnesium salicylate as well as those NSAIDs disclosed in the "Physicians Desk Reference" (1992 edition) whose contents are incorporated by reference herewith. The preferred steroidals are prednisone, prednisolone etc.

Additionally, thalidomide can be combined with or administered with β-amyloid inhibitors and with pentoxyphylline. The amount of thalidomide is typically from about 100 mg to about 500 mg and the amount of the β-amyloid inhibitors is from about 50 mg to 1000 mg. In the case of pentoxyphylline, the amounts are in the range of about 50 mg to 500 mg.

Within the context of the present specification, apolipoprotein E may refer to apolipoprotein E2, E3 or E4 or any combination thereof.

In another aspect of the invention thalidomide is combined with agents that suppress or reduce expression of apolipoprotein E alleles on chromosome 19.

Furthermore, thalidomide is administered with or combined with agents that eliminate or reduce the level of apolipoprotein E in the circulatory system.

In a further aspect of the invention, thalidomide is administered with or combined with agents that ameliorate the effect of apolipoprotein E or apolipoprotein E and amyloid deposits in the form of extracellular senile plaques, vascular amyloid deposits and neurofibrillary tangles, in the brain.

Thalidomide is also administered with or combined with apolipoprotein J, which may prevent deposition of beta amyloid into brain tissue.

Additionally thalidomide is adminsistered with or combined with agents that facilitate and/or maintain the solubility of beta amyloid.

Thalidomide is further administered with or combined with agents that prevent or reduce binding or reduce avidity of binding between apolipoprotein E and beta amylid.

Thalidomide is also administered with or combined with agents that prevent deposition of amyloid deposits in the brain.

Furthermore thalidomide is administered with or combined with agents that stimulate production of apolipoprotein J.

Other therapeutic combinations include:

Thalidomide with agents that prevent or reduce apolipoprotein E from binding to neurofibrillary tangles in brain tissue.

Thalidomide with agents that reduce or prevent development of neurofibrillary tangles in brain tissue.

Thalidomide with agents that prevent or reduce production of TAU protein, a component of neurofibrillary tangles.

Of course, the amounts of each compound selected will depend on the weight of the mammal and the disease state. One skilled in the art can adjust the dosage forms to achieve the desired therapeutic levels.

The compound of the present invention can be prepared and administered in a wide variety of oral and parenteral dosage forms. It will be obvious to those skilled in the art that the following dosage forms may comprise as the active component, either thalidomide alone or in combination with other compounds.

Preferably the compounds of the present invention are administered orally, intramuscularly or subcutaneously.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methycellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is also possible to administer thalidomide in a time-release formulation. A wide variety of methods are now available in the art for preparing time-release or long-acting compositions. Any of these time-release or long-acting formulations are suitable in the practice of the present invention as long as it does not adversely affect the effectiveness of the thalidomide in the treatment of cholinergic deficit states. Advantages of time-release formulations include a lower concentration of peak serum absorption which substantially reduces the adverse side effects and toxicity of the compound administered. In addition, a reduced frequency of administration results, which substantially improves patient compliance. A frequency of administration of every 12 or 24 hours would be preferred. In addition, more constant serum concentration of thalidomide would result thereby allowing a more consistent relief of symptoms.

The following examples, not to be construed as limiting, illustrate formulations which can be made according to the invention.

EXAMPLE 1

500 mg of thalidomide are mixed with 200 mg of ibuprofen. The active ingredients are triturated and q.s. with lactose to selected capsules size.

EXAMPLE 2

500 mg of thalidomide are mixed with 375 mg of naproxen. The active ingredients are triturated and q.s. with lactose to selected capsule size.

EXAMPLE 3

250 mg of thalidomide are mixed with 100 mg of tacrine. The active ingredients are triturated and q.s. with lactose to selected capsule size.

The following Examples further illustrate the usefulness of the invention.

EXAMPLE 4

Pinched off nerve endings (symptoms) from whole rat brain are first incubated in the presence of the precursor $^3$H-Choline, which is converted intracellularly to $^3$H-Acetylcholine (ACh). The release of ACh from synaptosomes is quantitated under low [K] and high [K] conditions intended to simulate physiological stimulation. The thalidomide or combinations with other drugs are tested under the above conditions.

EXAMPLE 5

Study Protocol and General Procedures

Five healthy volunteers of both sexes aged 60–75 years are admitted to a single blind study. Patients underwent the following procedures in a random way:

1. Baseline: registration of EEG (electroencephalogram), psychometric testing (short term memory), assessment of P-300 potential by audiometric testing.
2. The same after placebo (saline).
3. The same after thalidomide.

Each of phases 1 to 3 is followed by a period of at least one week before starting the next one.

Every patient undergoes all 3 phases.

Dosage

Thalidomide—250 mg four times daily. Saline: physiological concentration.

Memory test (short term memory)

The memory test consists in the memorization of a list of neutral words. The investigator reads the words; then a dispersion phase ensued, consisting in the performance of some arithmetical tasks. The subject is then asked to repeat as many words from the list as he/she could remember: The words used in each case were different, in order to avoid learning.

Attention Test

The aim of this test is to study the evoked potential P-300, known to be related with the attention span required to follow up and memorize a phenomenon.

The stimulus selected for this test is an auditive one, since audiometric testing of this potential has proven to be easy to perform and reliable. After a stimulus, a sound in this case, the mechanisms involved in the process of the hearing itself produce some bioelectric activity directly related to the stimulus itself. The perception process is more complex that the mere "hearing" and even after the stimulus has been removed, bioelectric activity related to it can be observed, as a form of 'echoes.' These 'echoes' are the evoked potentials. P-300 is a positive wave that can be observed 300 milliseconds after the first peak due to stimulus, and it is known to be related with the conscious processing of it, namely with the attention devoted to it.

The subject hears some beeps of either 1000 or 2000 hertz, given in a random way. He is then asked to say how many high beeps (2000 hertz) were sent.

EEG Monitoring

EEG monitoring starts one week after administration.

Duration of the Session

Each session lasts about one hour.

EEG Mapping

This was performed with a PATHFINDER device. A first screening of the maps for each frequency band (alpha, beta 1, beta 2, delta and theta) was performed, as well as for P-300.

Changes are defined as any variation in amplitude (potential) or in topographical distribution of the bands and are studied subject by subject, comparing the pattern obtained after injection of the products versus baseline recording and versus placebo.

From the foregoing description, one skilled in the art can easily ascertain the essential characteristics of this invention, and without departing from the spirit and scope thereof, can make various changes modifications of the invention to adapt it to various usages and conditions.

COMPOSITE ASSESSMENT

The Alzheimer's Disease Assessment Scale (ADAS) provides a composite assessment of all of the common symptoms of Alzheimer's disease. Evaluates cognitive and noncognitive behaviors. Scale is divided into two sections: an 11-team cognitive subscale that rates mood, vegetative functions, agitation, delusions, hallucinations, and concentration and distractibility. Scores on the cognitive subscale rante from 0-70 and on the noncognitive subscale from 0-50, with the higher scores indicating poorer performance. Used in logitudinal investigations and clinical trails. In clinical trials, only the cognitive subscale is typically used as a primary outcome measure. Score on the ADAS have been shown to correlate moderately with neurochemical markers or Alzheimer's disease. Some training required to administer the ADAS.

The Mini-Mental State Examination (MMSE) is a series of short tests that determine orientation, registration, attention, calculation ability, and recall, language and praxis. Widely used for dementia screening. Most appropriate for documenting cognitive dysfunction. Simple and can be rapidly administered. MMSE score of 23 or lower is used as an indication of sufficient cognitive decline for the diagnosis of dementia.

What is claimed is:

1. A method of treating the symptoms of cognitive decline in a mammal, which comprises administering to a mammal affected with said cognitive decline a therapeutically effective amount of thalidomide.

2. A method of treating a mammal suffering from memory impairment associated with aging comprising administering to said mammal suffering from memory impairment a therapeutically effective amount of thalidomide.

3. A method of treating the symptoms of cognitive decline in a mammal which comprises administering to a mammal affected with cognitive decline a therapeutically effective amount of a mixture of thalidomide with a compound selected from the group consisting of tacrine, non-steroidal anti-inflammatory carboxylic acids (NSAIDs), steroidal anti-inflammatory agents (SAIDs), $\beta$-amyloid inhibitors, pentoxyphylline, apolipoprotein $\epsilon$ agents and a pharmaceutically acceptable inert carrier.

4. The method of claim 3 wherein said NSAID is an aryl propionic acid.

5. The method of claim 3 wherein said NSAID is an aryl acetic acid.

6. The method of claim 4 wherein said aryl propionic acid is ibuprofen.

7. The method of claim 4 wherein said aryl propionic acid is naproxen.

8. The method of claim 4 wherein said aryl propionic acid is ketoprofen.

9. The method of claim 5 wherein said aryl acetic acid is indomethacin.

10. The method of claim 3 wherein said mixture comprises thalidomide, tacrine and a pharmaceutical inert carrier.

11. The method of claim 3 wherein said steroidal anti-inflammatory is prednisone.

12. The method of claim 3 wherein said steroidal anti-inflammatory is prednisolone.

13. A method for treating a central nervous system or peripheral nervous system cholinergic deficit state in a mammalian organism in need of such treatment, said method comprising administering to said mammal an amount of thalidomide effective in the treatment of a cholinergic deficit state and for a time sufficient to achieve a suitable blood level to treat said cholinergic deficit state.

14. The method of claim 13, comprising administering from about 30 mg to about 800 mg gram of said thalidomide per 24 hours.

15. The method of claim 14 further including a pharmaceutically acceptable inert carrier therefor.

16. The method of claim 14, comprising administering from about 100 mg to about 800 mg of said thalidomide per 24 hours.

17. The method of claim 13 further including a compound selected from the group consisting of non-steroidal anti-inflammatory carboxylic acids, steroidal anti-inflammatory agents, tacrine, $\beta$-amyloid inhibitors, pentoxyphilline and apolipoprotein $\epsilon$ agents.

18. The method of claim 17 wherein said non-steroidal anti-inflammatory carboxylic acid is ibuprofen.

19. The method of claim 17 wherein said nonosteroidal anti-inflammatory carboxylic acid is naproxen.

20. The method of claim 17 wherein said non-steroidal anti-inflammatory carboxylic acid is aspirin.

21. The method of claim 17 wherein said non-steroidal anti-inflammatory carboxylic acid is ketoprofen.

22. The method of claim 13 further including an apolipoprotein inhibitor.

23. A method for treating Alzheimer's disease in a mammal, said method comprising administering to said mammal about 30 mg to about 1 gram per 24 hours of thalidomide and a pharmaceutically acceptable inert carrier therefor.

24. A pharmaceutical composition of matter for treating central nervous system or peripheral nervous system cholinergic deficit states in a mammalian organism in need of such treatment, said composition comprising: (a) a unit dosage amount of thalidomide; (b) an additional therapeutic agent selected from the group consisting of prednisone, prednisolone tacrine and non-steroidal anti-inflammatory carboxylic acids, and a pharmaceutical acceptable inert carrier.

25. The pharmaceutical composition of claim 24 wherein said non steroidal anti-inflammatory carboxylic acid (NSAID) is selected from the group consisting of the propionic acids, the acetic acids, the fenamic acids and the biphenyl carboxylic acids.

26. The pharmaceutical composition of claim 25 wherein said NSAID is an aryl propionic acid.

27. The pharmaceutical composition of claim 26 wherein said NSAID is ibuprofen.

28. The pharmaceutical composition of claim 25 wherein said NSAID is selected from the group consisting of indoprofen ketoprofen, naproxen, benoxaprogen, flurbiprofen, fenoprofen, fenbufen, pirprogen, carprofen, oxaprozin, pranoprofen, miroprofen, tioxaprofen, suprofen, alminoprofen, tiaprofen, fluprofen, bucloxic acid, sulindac, tolmetin, zomepirac, diclofenac, fenclofenac, alclofenac, ibufenac, isoxepac, furofenac, tiopinac, zidometacin, acematacin, fentiazac, clidanac, oxpinac, fenflozic acid, mefanamic acid, meclofenamic acid, flufenamic acid, niflumic acid, and tolfenamic acid.

* * * * *